US 6,581,615 B2

(12) United States Patent  
Kaketani et al.

(10) Patent No.: US 6,581,615 B2
(45) Date of Patent: Jun. 24, 2003

(54) APPARATUS FOR WASHING AND DISINFECTING AN ENDOSCOPE CABLE ASSEMBLY

(76) Inventors: Kazutoshi Kaketani, Imatsuru-3-chome-7-8, Ohita-shi, Ohita-ken (JP); Osamu Emoto, Hadaue-3-kumi, Ohita-shi, Ohita-ken (JP)

(*) Notice: Subject to any disclaimer, the term of this patent is extended or adjusted under 35 U.S.C. 154(b) by 131 days.

(21) Appl. No.: 09/809,417

(22) Filed: Mar. 16, 2001

(65) Prior Publication Data
US 2001/0042561 A1 Nov. 22, 2001

(30) Foreign Application Priority Data

Mar. 29, 2000 (JP) .................................. 2000-132953
Nov. 8, 2000 (JP) .................................. 2000-378146

(51) Int. Cl.[7] ............................................... B08B 3/02
(52) U.S. Cl. .......................... 134/22.12; 134/168 C; 134/170; 134/182; 134/169 C
(58) Field of Search .......................... 134/166 C, 169 C, 134/167 C, 168 C, 170, 182, 169 R, 22.1, 22.11, 22.12, 22.18

(56) References Cited

U.S. PATENT DOCUMENTS

| 3,963,438 A | * | 6/1976 | Banez |
| 4,064,886 A | * | 12/1977 | Heckele |
| 4,288,882 A | * | 9/1981 | Takeuchi |
| 4,763,678 A | * | 8/1988 | Ott |
| 5,090,433 A | * | 2/1992 | Kamaga |
| 5,186,194 A | * | 2/1993 | Kitajima |
| 5,288,467 A | * | 2/1994 | Biermaier |
| 5,494,637 A | * | 2/1996 | Barlow |

FOREIGN PATENT DOCUMENTS

| JP | 11-70069 | * | 3/1996 |
| JP | 11-19025 | * | 1/1999 |
| WO | WO98/29028 | * | 7/1998 |

* cited by examiner

Primary Examiner—Frankie L. Stinson
(74) Attorney, Agent, or Firm—Stevens, Davis, Miller & Mosher, LLP (57) ABSTRACT

To completely disinfect a soft cable and a forceps hole of the used endoscope.

An apparatus for washing and disinfecting an endoscope cable assembly wherein a U-shaped pipe washing pipe 3 for supplying strong alkaline water, strong acidic water and water in said order is provided on a box 1, an insert port x2 for inserting an inset part 9b of an endoscope is provided in one end of the U-shaped pipe washing pipe 3, and a storing part 2, an overflow part 7 and an overflow plate 4 are provided thereon, the other end thereof being projected from the upper end of a soft cable 12 inserted into the U-shaped pipe washing pipe 3, the inside diameter d1 of the U-shaped pipe washing pipe 3 is made larger than the outside diameter of the soft part cable 12, and the radius of curvature y of the U-shaped pipe washing pipe 3 is buckled while causing the soft part cable 12 to overflow washing water from the overflow plate 4 and while receiving buoyancy thereof, and setting being made so as not to come in contact with the wall surface of the U-shaped pipe washing pipe 3.

7 Claims, 8 Drawing Sheets

APPARATUS FOR WASHING AND DISINFECTING AN ENDOSCOPE CABLE ASSEMBLY

BACKGROUND OF THE INVENTION

1. Field of the Invention

The present invention relates to an apparatus for washing and disinfecting an endoscope cable assembly.

2. Related Art

Most of conventional automatic endoscope washing methods use chemicals of a glutaric aldehyde base within a disinfecting apparatus, and therefore an endoscope is dipped therein for a predetermined time after which the endoscope is washed. In this method, however, a foul odor of glutaric aldehyde remains in the endoscope even after washing, making it difficult to think that the endoscope was completely washed.

In consideration of toxicity of glutaric aldehyde relative to the human body, even if disinfection of the endoscope is complete, it is not completely safety.

Further, sometimes, an operator engaged in washing and disinfecting an endoscope feels ill due to the foul odor, or suffers from occurrence of bronchitis and dermatitis due to allergy with respect to glutaric aldehyde.

Furthermore, if the used glutaric aldehyde causes to flow into a drainage, its toxicity may affect on natural environments.

Attention has been paid to the disinfecting force of strong acidic water since several years, which begins to be used often in medical facilities and food-handing facilities. However, the strong acidic water has a disadvantage in that when it comes in contact with an organic matter, its disinfecting force is rapidly lost.

However, the strong acidic water is free from toxicity to the human body and has slight chlorine odor, which is used for medical treatment of allergy, is excellent in disinfecting effect, is safety, and involves no breakage of natural environments.

Recently, an endoscope washing and disinfecting apparatus using strong acidic water is being sold, which is a washing and disinfecting apparatus which filtrates again the strong acidic water used once for washing and disinfecting an endoscope to reproduce and use it, and merely serves to wash and disinfect a tube-insert portion of an endoscope to a patient. Apparatuses in consideration of washing and disinfecting an operating part are limited to a few apparatuses using glutaric aldehyde.

This will not solve a disadvantage that an organic matter, particularly, mucus or blood is mixed to thereby lose the disinfecting effect, and a little uneasy remains as an endoscope washing and disinfecting apparatus, and the possibility of secondary infection to a patient cannot be denied unless washing and disinfection including the operating part of an endoscope are taken into consideration.

In view of the foregoing, an endscope washing and disinfecting apparatus of an overflow type was developed which takes consideration so as not to give rise to occurrence of a disadvantage involved in strong acidic water at the time of washing and disinfection.

SUMMARY OF THE INVENTION

The apparatus according to the present invention is summarized as follows:

A U-shaped pipe washing pipe 3 for supplying strong alkaline water, strong acidic water and water in order is provided on a box 1, an insert port x2 for inserting an insert part 9d of an endoscope is provided in one end of the U-shaped pipe washing pipe 3, and a storing part 2, an overflow part 7 and an overflow plate 4 are provided thereon, the other end thereof being projected from the upper end of a soft cable 12 inserted into the U-shaped pipe washing pipe 3, the washing pipe has two channels, a first channel passing outside of the soft part cable 12 inserted into the U-shaped pipe washing pipe 3, further reaching the overflow part 7, and overflowing from the overflow plate 4 to the overflow part 7, a second channel entering a forceps from the upper end of the other end of the soft part cable 12, and reaching a suction type forceps washing device 12 connected to a suction clasp 10a, the inside diameter d1 of the U-shaped pipe washing pipe 3 is made larger than the outside diameter of the soft part cable 12, and the radius of curvature y of the U-shaped pipe washing pipe 3 is buckled while causing the soft part cable 12 to overflow washing water from the overflow plate 4 and while receiving buoyancy thereof, and setting being made so as to not come in contact with the wall surface of the U-shaped pipe washing pipe 3.

First, mucus, blood and the like adhered to the soft part cable 12 and the forceps hole 12a are washed in the overflow manner with strong alkaline water, and afterwards washed with strong acidic water, whereby the disinfection effect of the strong acidic water can be maintained. The forceps hole 12a can be reused immediately since it is finally dried by absorbing air from the suction port 17. Further, if drained, the strong acidic water and strong alkaline water are returned to water, thus not affecting on the natural environment.

The washing effect of the overflow type endoscope washing and disinfecting apparatus is eminent, and even in a bacterium culture inspection of an endoscope after washing and a bacterium culture inspection of endoscope washing and disinfecting apparatus, bacterium indicative of pathogenity has not been observed. Since washing pipe 3 is in the shape of U, the washing operation is simple and quick. Particularly, washing of the outer circumference of the soft part cable 12 causes washing water to overflow constantly whereby operation is carried out quickly and perfectly.

The washing effect of the apparatus of the present invention will be described with reference to FIG. 9. Let y be the radius of curvature of the washing pipe 3 in the apparatus of the present invention.

Figure 9:
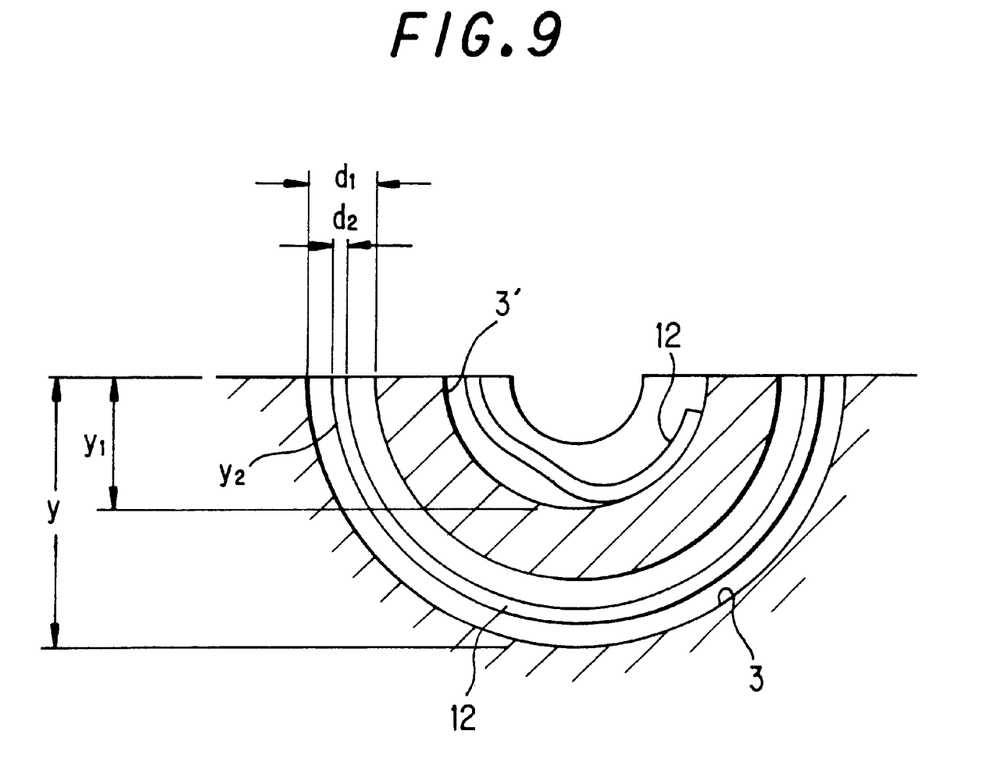
FIG. 9 is a view for explaining operation of the present invention.

As shown in FIG. 9, the case of the radius of curvature y1 of an imaginary washing pipe 3' will taken into consideration. In this case, in the case of the radius of curvature y1, the buckling properties of the soft part cable 12 are small from a viewpoint of the buckling properties of the soft part cable 12, and therefore, the soft part cable 12 becomes buckled into contact with the wall surface of the washing pipe 12.

In this case, washing cannot be done with respect to the portion in which the cable 12 comes in contact with the wall surface. On the other hand, in the case of the radius of curvature y as in the present invention, the cable 12 can be buckled due to its buckling properties without contacting the wall surface of the washing pipe 3. At that time, of course, the buoyancy caused by washing water is applied to the soft part cable 12. Since at that time, the washing water constantly overflows from the overflow plate 4, the buoyancy applied to the soft part cable 12 is substantially constant.

That is, in the present invention, the cable 12 receives the buoyancy of washing water whereby the radius of curvature y by a portion not to contact with the wall surfaces of the washing pipe 3 is set.

A relationship between the inside diameter d1 and the outside diameter d2 of the soft part cable 12 is considered to be as follows: (FIG. 8)

$$d1 \geq 2 \text{ to } 3 \text{ times of } d2$$

Preferably, the radius of curvature y and the inside diameter d1 of the washing pipe 3 is large, but actually, there is a limit because the washing box 1 becomes excessively large in terms of design.

BRIEF DESCRIPTION OF THE DRAWINGS

FIG. 3(a) is a side sectional view of the using condition of an endoscope. and (b) being a sectional view thereof;

DESCRIPTION OF THE PREFERRED EMBODIMENTS

The apparatus according to the present invention will be described hereinafter with reference to FIGS. 1 to 9.

The apparatus according to the present invention is summarized as follows:

A U-shaped pipe washing pipe 3 for supplying strong alkaline water, strong acidic water and water in order is provided on a box 1, an insert port x2 for inserting an insert part 9d of an endoscope is provided in one end of the U-shaped pipe washing pipe 3, and a storing part 2, an overflow part 7 and an overflow plate 4 are provided thereon, the other end thereof being projected from the upper end of a soft cable 12 inserted into the U-shaped pipe washing pipe 3, the washing pipe has two channels, a first channel passing outside of the soft part cable 12 inserted into the U-shaped pipe washing pipe 3, further reaching the overflow part 7, and overflowing from the overflow plate 4 to the overflow part 7, a second channel entering a forceps from the upper end of the other end of the soft part cable 12, and reaching a suction type forceps washing device 12 connected to a suction clasp 10a, the inside diameter d1 of the U-shaped pipe washing pipe 3 is made larger than the outside diameter of the soft part cable 12, and the radius of curvature y of the U-shaped pipe washing pipe 3 is buckled while causing the soft part cable 12 to overflow washing water from the overflow plate 4 and while receiving buoyancy thereof, and setting being made so as to not come in contact with the wall surface of the U-shaped pipe washing pipe 3.

The U-shaped pipe washing pipe 3 is communicated with a water pipe 6.

Next, the using method will be described.

First, the soft part cable 12 is sunk into strong alkaline water and the U-shaped pipe washing pipe 3.

The strong alkaline water washes the outer circumference of the soft part cable 12 while overflowing on the overflow part 7, Water is drained from a communication hole 8 of the overflow part 7. At this time, the upper end of the soft part cable 12 is set somewhat lower than the upper end of the overflow plate 4.

First, the outer circumference of the soft part cable 12 of the endoscope 9 is washed with water, after which it is sunk into the washing pipe 3. Then, the outer circumference of the cable 12 is washed while pouring strong alkaline water into the washing pipe 3.

A forceps clasp 9c is placed over a forceps insert port. As a result, the forceps insert port 12a of the soft part cable 12 and the communication hole 11a of the forceps hole of a universal code 11 constitutes a series of channels.

A suction pump 13b in FIG. 3 is operated to absorb alkaline water within an alkaline V-shaped washing pipe 3 via forceps insert ports 11 and 12a. The absorbed alkaline water is drained from a drain pipe 13c in FIG. 3.

Thus, the outer circumference of the soft part cable 12 and the forceps hole 12a are washed. The alkaline water is constantly drained, during the washing, via the overflow part 7.

The similar step is carried out also with respect to strong acidic water.

In washing the forceps hole 12a, the above-described operation is carried out using first strong alkaline water, second strong acidic water, and third water, and fourth, air is absorbed from a suction box 13a to dry the forceps hole 12a. Of course, at this time, operation using water, strong alkaline water, and strong acidic water is terminated, and the washing pipe 3 is empty.

The apparatus according to the present invention will be described in detail hereinafter.

Figure 8A:
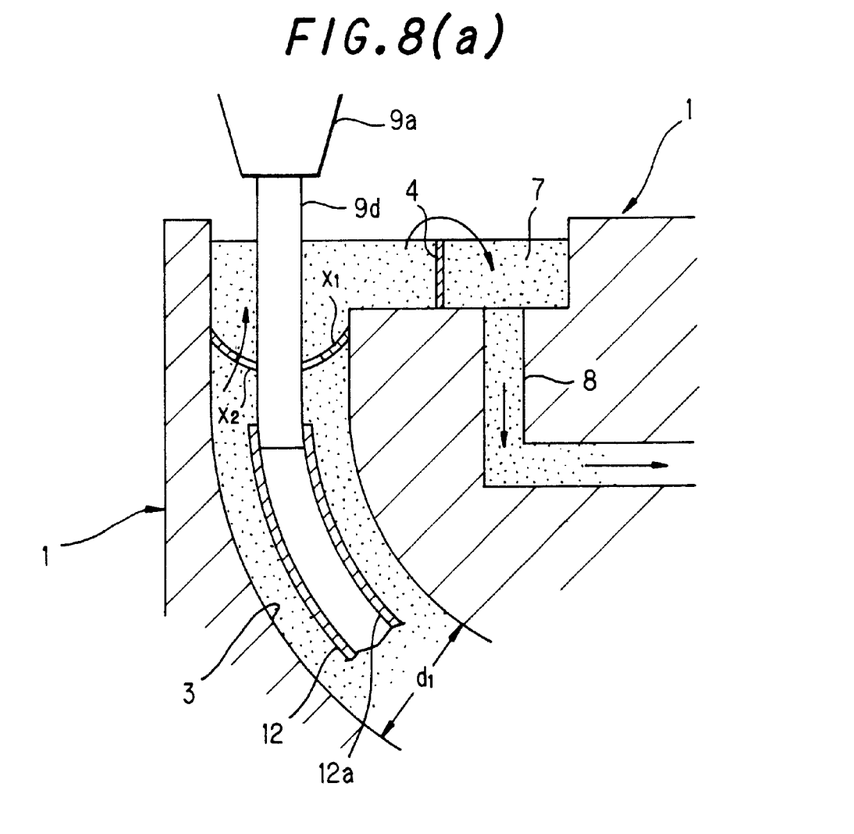
FIG. 8(a) is an enlarged sectional view of a storing part 2 portion in FIG. 2, and (b) being an enlarged view of an insert stop plate x2.
Figure 8B:
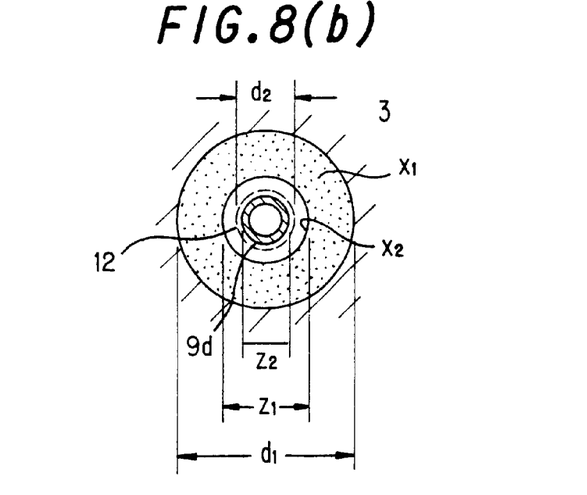

FIG. 8(b) is an enlarged view of the storing part 2 portion of FIG. 8(a).

A forceps insert port 9b is mounted at the lower part of a grip part 9a of an endoscope 9. It is inserted into an insert port x1 of an insert plate x2 of an inlet of the U-shaped pipe washing pipe 3. In an insert part 9d, a forceps clasp 9c is placed on the forceps insert port 9b. That is, at this time, a communication hole 11a of the forceps hole of a universal cord 11 is communicated with a forceps hole 12a of a soft part cable 12.

The U-shaped pipe washing pipe 3 has a large radius of curvature y, and the inside diameter d1 thereof is larger than the outside diameter d2 of the soft part cable 12.

A relationship between the inside diameter z1 of the insert hole x2 and the outside diameter z2 of the insert part 9b is as follows:

$$z1 > z2$$

That is, water in the U-shaped washing pipe 3 constantly continues to move up toward the storing part 2 from a clearance between the endoscope insert part 9b of the insert hole z2 as shown in FIG. 8.

When the radius of curvature y of the U-shaped washing pipe 3 is too small. it is difficult to insert the soft part cable 12 into the washing pipe 3, that is, the radius of curvature y of the U-shaped washing pipe 3 should be the radius of curvature y so that the soft part cable 12 may be easily inserted into the width thereof according to the elasticity of the cable. When the radius of curvature y is increased and the inside diameter d1 of the washing pipe 3 is increased whereby the soft part cable 12 assumes nearly a straight line to facilitate insertion of the endoscope insert part 9b into the washing pipe 3. If the radius of curvature y is 30 cm at a minimum, no contact with the wall surface of the washing pipe 3 occurs as shown in Table 1.

The result of test with respect to the radius of curvature y of the washing pipe 3 is as follows:

In FIG. 9, the radius of curvature y was measured externally of the pipe 3.

The test is conducted such that the inside diameter d1 of the pipe 2 is three times of the outside diameter d2 of the soft part cable 12. The soft part cable of an endoscope used are made of Olympus, Toshiba, and Asahi Optics, and their buckling properties are scarcely different.

| Radius of curvature (FIG. 9) (y) | Presence of contact of soft cable with wall surface of pipe 3 |
|---|---|
| 23 cm | Yes |
| 25 cm | Yes |
| 30 cm | No |
| 33 cm | No |
| 35 cm | No |

If the radius of curvature y of the washing pipe 3 is too small, the soft part cable 12 becomes close contacted the inner wall of the washing pipe 3, failing to completely wash the outer circumference thereof.

Figure 1:
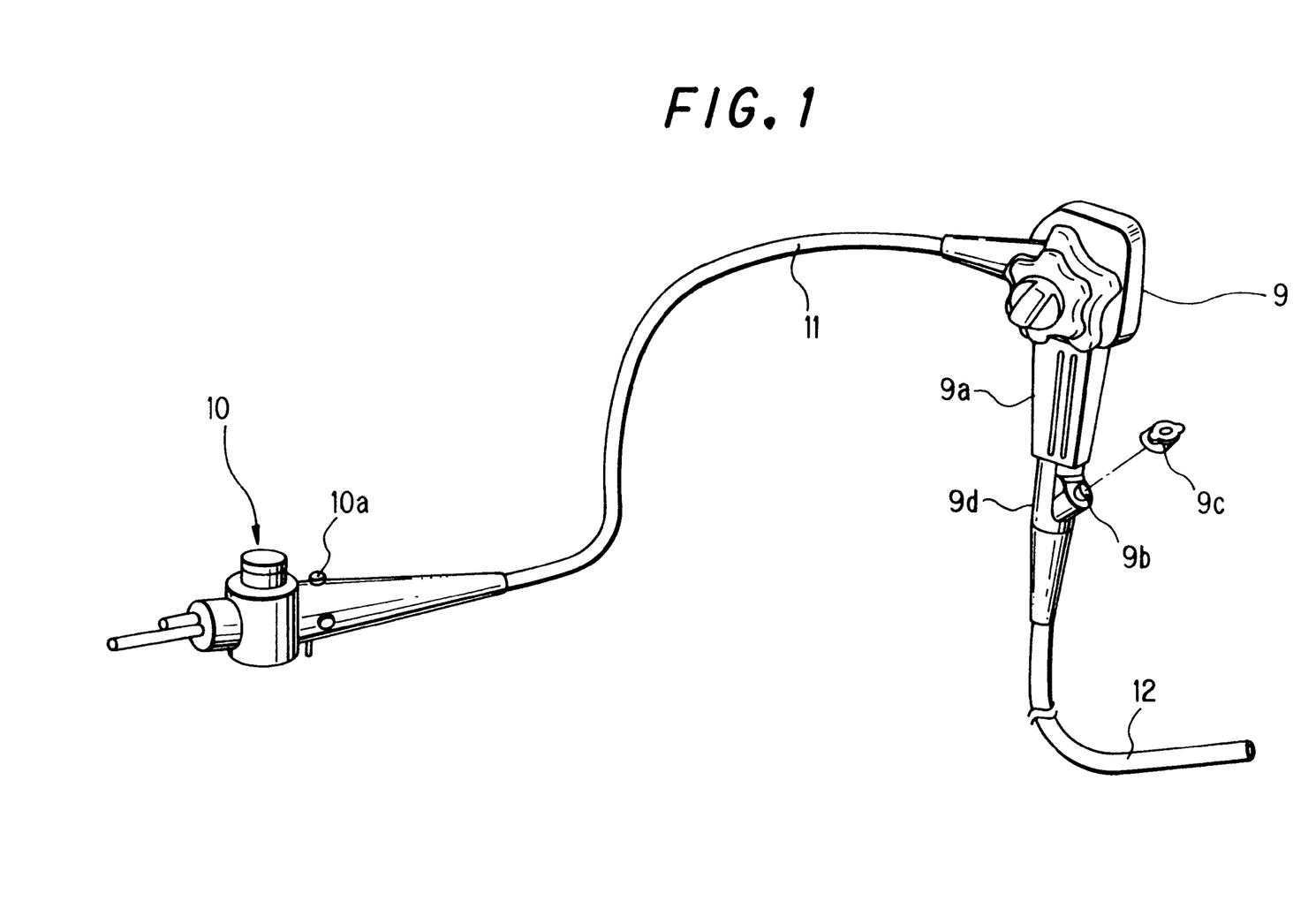
FIG. 1 is a perspective view of the whole endoscope.
Figure 2:
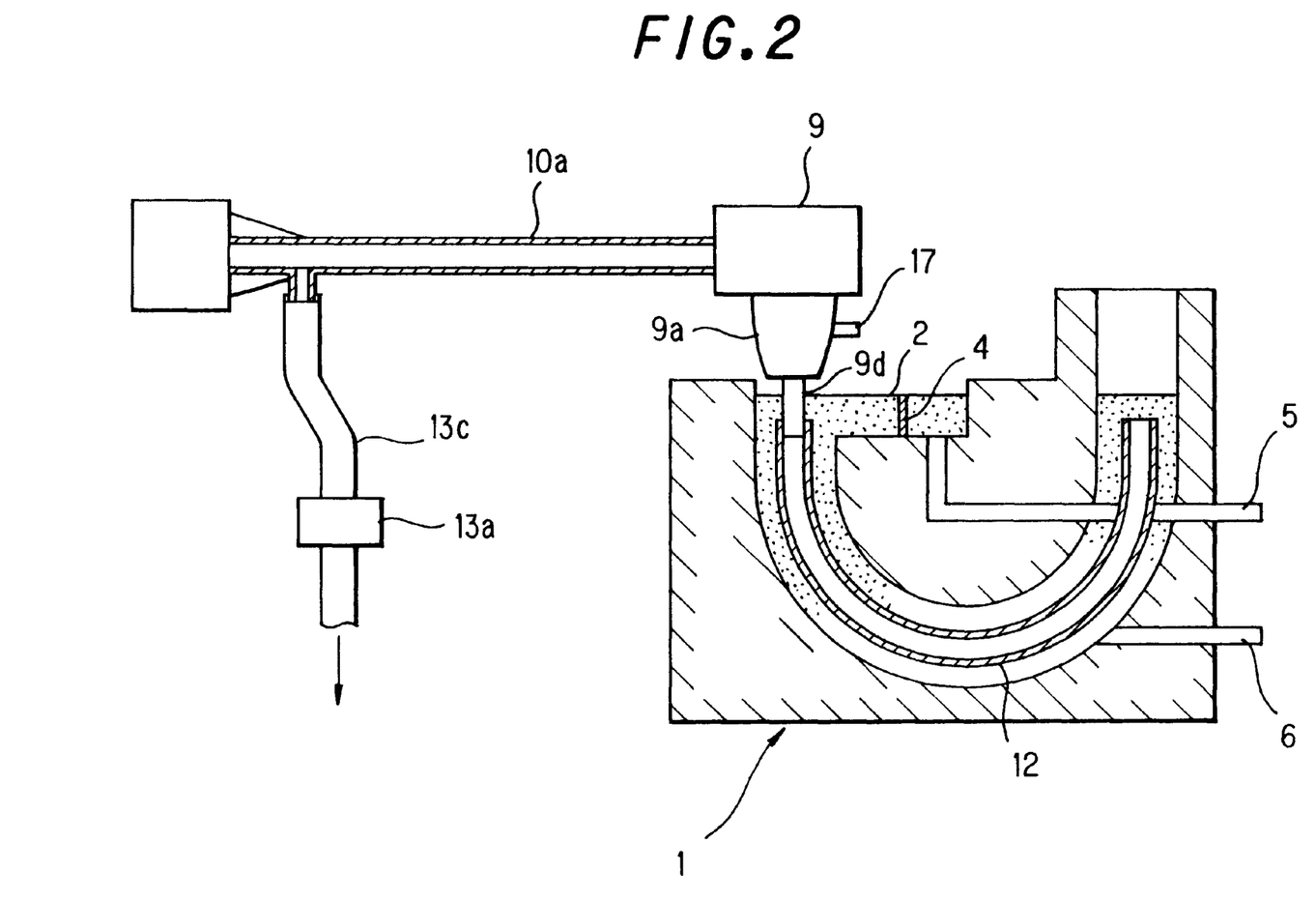
FIG. 2 is a side sectional view when a soft part cable is inserted into an endoscope washing apparatus.
Figures 3A, 3B:
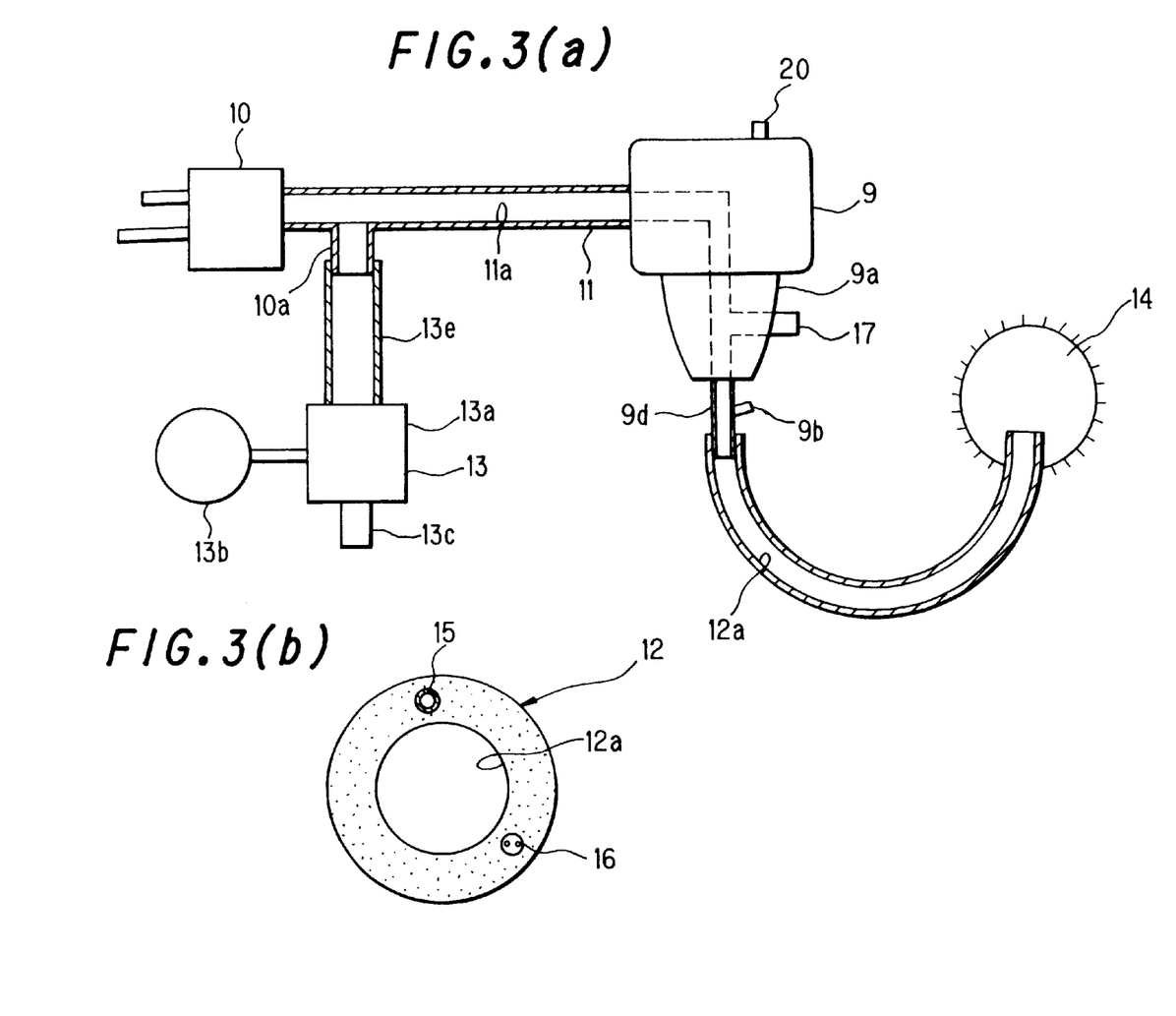

That is, in FIG. 2, and FIGS. 8(a) and (b), (1) It is desired that the radius of curvature y of the washing pipe 3 be as large as possible, (2) A relationship between the inside diameter z1 of the insert hole x2 and the outside diameter z2 of the insert part 9b is z1>z2

(3) It is desired that the inside diameter d1 of the washing pipe 3 be considerably larger than the outside diameter d2 of the soft part cable 12.

In this manner, water flowing into the washing pipe 3 constantly overflows Beyond the overflow plate 4 to uniformly wash the outer circumference of the soft part cable 12 and the forceps hole 12a.

At this time the suction box 13a of the forceps washing apparatus 13 continues to absorb water in the washing pipe 3 to wash the forceps hole 12a while overflowing the overflow plate, as shown in FIG 3.

The suction forceps port washing apparatus 13 will be described below with reference to FIG. 3.

The suction forceps port washing apparatus 13 used in the present invention comprises a suction box 13a, a suction pump 13b, an anti-reverse tube 13d, a suction clasp 10a, and a vinyl tube 13c. During the operation of the vacuum pump 13b, the anti-reverse tube 13d is operated, and washing liquid flows from the suction clasp 10a into the suction box 13a. At the time when the vacuum pump 13b ceases to operate, the vinyl tube 13e is pulled out of the suction clasp 10a or the switch of the vacuum pump 13b is turned off, and then the anti-reverse operation of the anti-reverse tube 13d is automotically released by water pressure of the suction box 13a so that water is drained. At this time, a suction part 17 and a forceps insert part 9b are closed.

As described above, there is an advantage that the suction forceps port washing apparatus 13 according to the present invention is powerful in the suction operation to the suction box 13a, and after washing, water is automatically drained. Finally, air is drawn from the suction port 17 (FIG. 3) to dry the forceps insert hole 12a.

Next, the process of development of the present invention will be described.

The characteristics of strong acidic water comprise strong disinfection effect and that if being drained after use, it is given back as water to the natural field. Further, the safety is high relative to the human body, and if the disadvantage the strong acidic water is merely recognized, it is possible to disinfect an endoscope safely, in a short period of time, and completely.

The present invention creates an endoscope washing and disinfecting apparatus which overcomes an disadvantage that when strong acidic water comes in contact with mucus or blood, the disinfection effect is rapidly lost, and improves the disinfection effect.

The endoscope washing and disinfecting apparatus according to the present invention employed an overflow system so that an endoscope being disinfected may always contact fresh strong acidic water.

Figure 4:
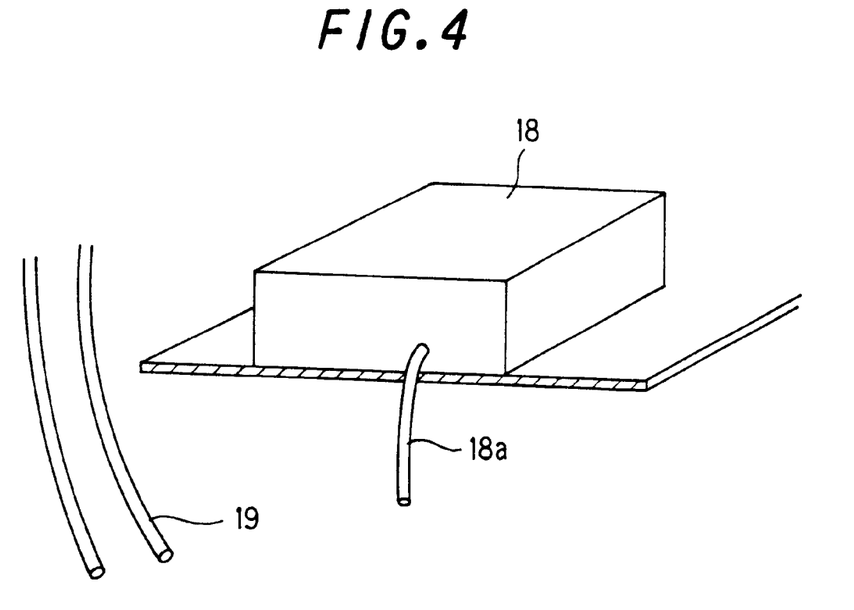
FIG. 4 is a perspective view of a washing box.
Figure 5:
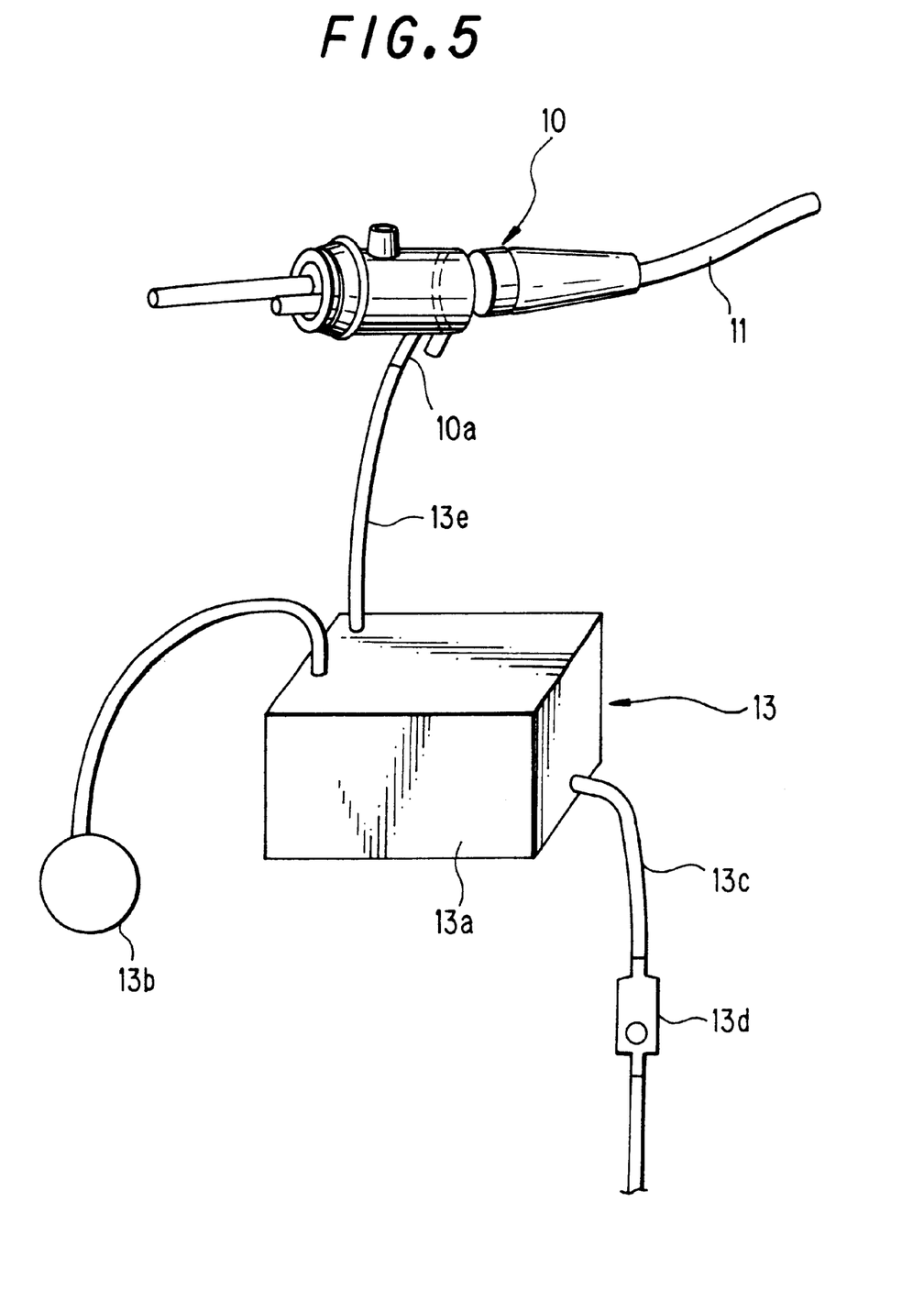
FIG. 5 is a perspective view of the using condition of a forceps washing apparatus.
Figure 6:
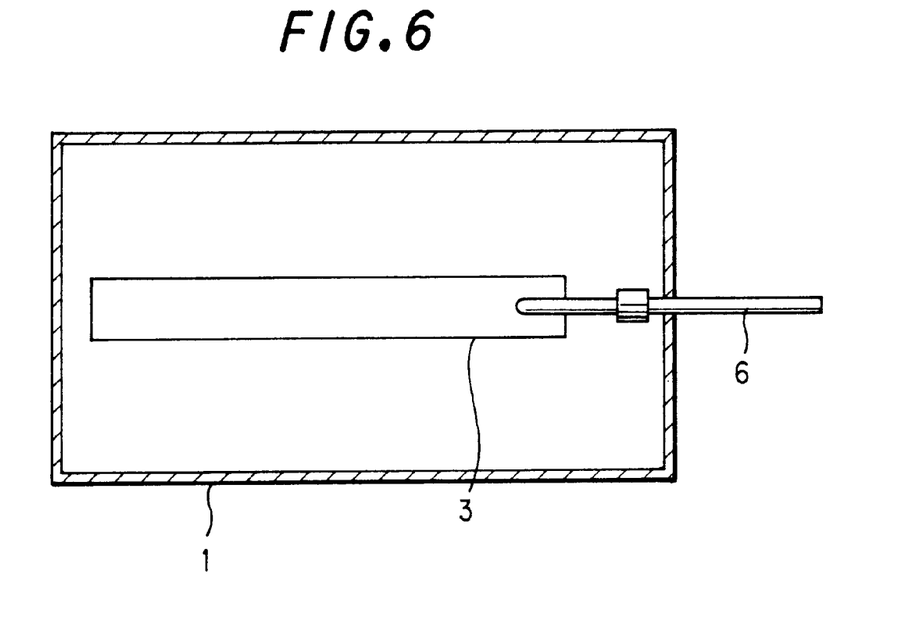
FIG. 6 is a bottom view of a washing apparatus.
Figure 7:
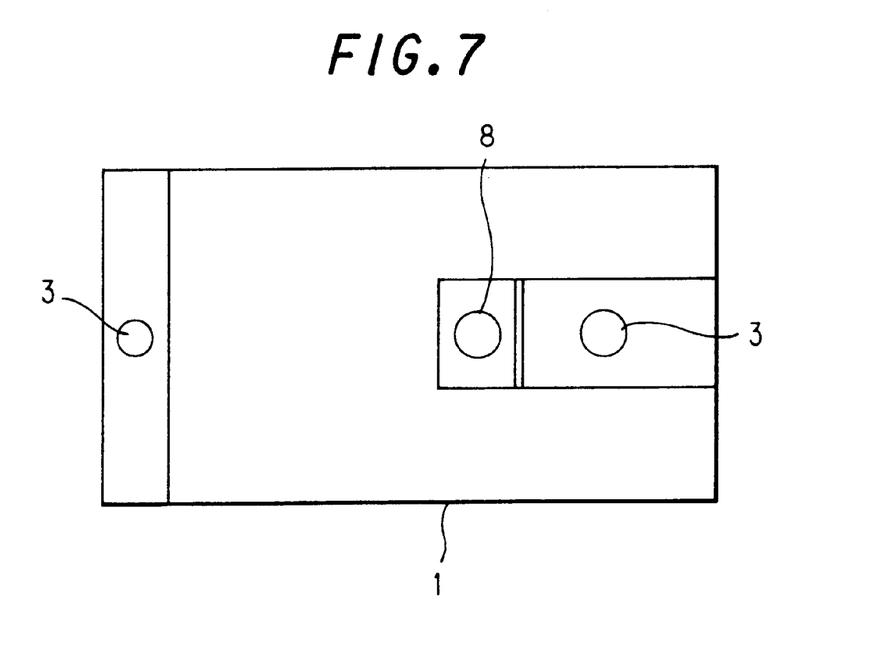
FIG. 7 is a plan view of a washing apparatus.

A curve in line with the flexibility of an endoscope is provided in order to make the size of the apparatus compact, and for adapting the whole size to a colon endoscope, the height and length are about 800 mm, and the width is about 350 mm, one example of which is shown in FIG. 4.

18 is electro chemical barrel. 18a is a pipe to supply strong alkalin, acidic water. 19 is a pipe to supply water. Further, in order to avoid the metal corrosion action caused by oxidization of strong acidic water, the apparatus uses a vinyl chloride plate, and a vinyl chloride pipe, and uses no metal at all.

Apparatuses used other than the washing and disinfection apparatus are as follows:

1) Washing apparatus for air and liquid

2) Washing apparatus for suction forces port (a suction pin having an automatic drain port attached to a small suction machine)

3) Strong acidic water generating apparatus

Actual Washing

In washing, after completion of inspection of a an endoscope, brushing is conducted with respect to the suction forceps port, and mucus or the like adhered to the periphery of the endoscope is simply washed away.

Standard is set up such that after water washing or three minutes, as shown in Table 1 washing is conducted by the developed endoscope washing apparatus using strong alkaline water for 30 seconds, strong acidic water or 90 seconds, and city water for 30 seconds.

Test for Residual Bacterium

For studying if the soft part cable 12 of an endoscope is washed and disinfected by the apparatus of the present invention, test was conducted with respect to 30 examples as shown in Table 1. In 30 examples, bacterium is cultured in advance to the surface of the cable 12.

TABLE 1

Disinfection effect of strong acidic water (pH 2.5, chlorine concentration 50 ppm)

| Case | Bacterium Detection | Case | Bacterium detection | Case | Bacterium detection |
|------|---------------------|------|---------------------|------|---------------------|
| 1    | (−)                 | 11   | (−)                 | 21   | (−)                 |
| 2    | (−)                 | 12   | (−)                 | 22   | (−)                 |
| 3    | (−)                 | 13   | (−)                 | 23   | (−)                 |
| 4    | (−)                 | 14   | (−)                 | 24   | (−)                 |
| 5    | (−)                 | 15   | (−)                 | 25   | (−)                 |
| 6    | (−)                 | 16   | (−)                 | 26   | (−)                 |
| 7    | (−)                 | 17   | (−)                 | 27   | (−)                 |
| 8    | (−)                 | 18   | (−)                 | 28   | (−)                 |
| 9    | (−)                 | 19   | (−)                 | 29   | (−)                 |
| 10   | (−)                 | 20   | (−)                 | 30   | (−)                 |

If the endoscope washing apparatus of the overflow system making use of strong acidic water from the culture tests as described above is used with pH 2.4 to 2.4 and 5.0 to 6.0 ppm of chlorine concentration of strong acidic water, the disinfection effect is great.

It is necessary for using strong acidic water for washing and disinfection of an endoscope to wash with strong acidic water as large amount as possible with pH 2.5 or less and chlorine concentration 50 ppm or more. For overcoming a disadvantage of strong acidic water that said to lose effect by contact of mucus or blood with an organic matter, a doubt remains in disinfection effect in case of the stored water system washing and disinfection, but in the overflow system, the endoscope always comes in contact with fresh strong acidic water.

It is desired in the washing and disinfection of an endoscope that the whole endoscope be disinfected, but at least the insert part and the operating part need be disinfected.

What is claimed is:

1. An apparatus for washing and disinfecting an endoscope cable assembly comprising:
    a U-shaped pipe washing pipe 3 for supplying strong alkaline water, strong acidic water and water in order which is provided on a box 1,
    an insert port x2 for inserting an insert part 9d of an endoscope is provided in one end of the U-shaped pipe washing pipe 3, and a storing part 2, an overflow part 7 and an overflow plate 4 are provided thereon,
    the other end thereof being projected from the upper end of a soft cable 12 inserted into the U-shaped pipe washing pipe 3,
    the washing pipe has two channels,
    a first channel passing outside of the soft part cable 12 inserted into the U-shaped pipe washing pipe 3, further reaching the overflow part 7, and overflowing from the overflow plate 4 to the overflow part 7,
    a second channel entering a forceps from the upper end of the other end of the soft part cable 12, and reaching a suction type forceps washing device 12 connected to a suction clasp 10a,
    the inside diameter d1 of the U-shaped pipe washing pipe 3 is made larger than the outside diameter of the soft part cable 12, and the radius of curvature y of the U-shaped pipe washing pipe 3 is buckled while causing the soft part cable 12 to overflow washing water from the overflow plate 4 and while receiving buoyancy thereof, and
    setting being made so as the cable assembly does not come in contact with the wall surface of the U-shaped pipe washing pipe 3.

2. The apparatus for washing and disinfecting an endoscope cable assembly according to claim 1, wherein the second channel of the washing pipe is connected to a suction clasp 10a to be able to absorb open air in the suction box 13a, and absorbs air for drying the forceps hole 12a, after terminating the supplying of the strong alkaline water, the strong acidic water, and the water.

3. An apparatus for washing and disinfecting an endoscope cable assembly comprising:
    a U-shaped washing pipe comprising:
        a channel disposed therein;
        first and second opposed ends;
        an insert port, for receiving at least a part of the endoscope to be washed and disinfected, disposed at the first end, the insert port comprising an overflow assembly; and
    a suction device,
    wherein the shape of the washing pipe is such that when the endoscope is inserted inside the channel of the washing pipe, and connected at a first terminus to the suction device, the endoscope does not contact the interior walls of the washing pipe.

4. The apparatus for washing and disinfecting an endoscope cable assembly according to claim 3, wherein the washing pipe has a radius of curvature (y) greater than or equal to 30 cm.

5. The apparatus for washing and disinfecting an endoscope cable assembly according to claim 4, wherein the washing pipe has a radius of curvature (y) of between 30 and 35 cm.

6. The apparatus for washing and disinfecting an endoscope cable assembly according to claim 3, wherein the channel of the washing pipe has an inside diameter ($d_1$) three times an outer diameter of the soft part cable ($d_2$).

7. A method for washing and disinfecting an endoscope comprising:
    providing the apparatus of claim 3;
    inserting an insert part of an endoscope into the insert port, such that a soft part cable of the endoscope extends from the insert port substantially to the second end of the washing pipe and such that the soft part cable does not contact the interior wall of the washing pipe;
    introducing, strong alkaline water into the washing pipe, such that the strong alkaline water washes the outer surface of the soft part cable and enters a hole in an end of the soft part cable;
    suctioning at least part of the strong alkaline water through the endoscope via the hole in the soft part cable;
    removing the remaining strong alkaline water from the washing pipe through the overflow assembly;
    introducing, strong acidic water into the washing pipe, such that the strong acidic water washes the outer surface of the soft part cable and enters the hole in the end of the soft part cable,
    suctioning at least part of the strong acidic water through the endoscope via the hole in the soft part cable;
    removing the remaining strong acidic water from the washing pipe through the overflow assembly;
    introducing, neutral pH water into the washing pipe, such that the neutral pH water washes the outer surface of the soft part cable and enters the hole in the end of the soft part cable,
    suctioning at least part of the neutral pH water through the endoscope via the hole in the soft part cable; and
    removing the remaining neutral pH water from the washing pipe through the overflow assembly.

* * * * *